(12) United States Patent
Cheng et al.

(10) Patent No.: US 9,570,299 B1
(45) Date of Patent: Feb. 14, 2017

(54) FORMATION OF SIGE NANOTUBES

(71) Applicant: International Business Machines Corporation, Armonk, NY (US)

(72) Inventors: Kangguo Cheng, Schenectady, NY (US); Hong He, Schenectady, NY (US); Ali Khakifirooz, Los Altos, CA (US); Juntao Li, Cohoes, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/847,619

(22) Filed: Sep. 8, 2015

(51) Int. Cl.
| | | |
|---|---|---|
| *H01L 21/02* | (2006.01) | |
| *H01L 21/306* | (2006.01) | |
| *H01L 21/324* | (2006.01) | |
| *H01L 29/06* | (2006.01) | |
| *H01L 29/161* | (2006.01) | |

(Continued)

(52) U.S. Cl.
CPC ....... *H01L 21/02694* (2013.01); *G01N 33/005* (2013.01); *G01N 33/0036* (2013.01); *H01L 21/02532* (2013.01); *H01L 21/02606* (2013.01); *H01L 21/02647* (2013.01); *H01L 21/30604* (2013.01); *H01L 21/324* (2013.01); *H01L 29/0649* (2013.01); *H01L 29/0669* (2013.01); *H01L 29/161* (2013.01); *B82Y 15/00* (2013.01); *B82Y 40/00* (2013.01); *Y10S 977/814* (2013.01); *Y10S 977/89* (2013.01); *Y10S 977/90* (2013.01); *Y10S 977/957* (2013.01)

(58) Field of Classification Search
CPC .................. H01L 21/02532; H01L 21/30604; H01L 21/02606; H01L 21/02647; H01L 29/0649; H01L 29/0669; H01L 29/161; H01L 21/02694; G01N 33/0036; G01N 33/005

See application file for complete search history.

(56) References Cited

U.S. PATENT DOCUMENTS

| | | | |
|---|---|---|---|
| 7,544,626 B2 | 6/2009 | Tang et al. | |
| 7,956,108 B2 | 6/2011 | Coleman et al. | |

(Continued)

FOREIGN PATENT DOCUMENTS

| | | | |
|---|---|---|---|
| IN | 5605CHE2014 A | 11/2014 | |
| IN | 201405605 | * 11/2014 | |

OTHER PUBLICATIONS

Schmidt et al., "Nanotechnology: Thin solid films roll up into nanotubes," Nature 410, p. 168 (Mar. 2001).

(Continued)

*Primary Examiner* — Minh-Loan Tran
*Assistant Examiner* — Farid Khan
(74) *Attorney, Agent, or Firm* — Vazken Alexanian; Michael J. Chang, LLC (57) ABSTRACT

Techniques for forming nanostructured materials are provided. In one aspect of the invention, a method for forming nanotubes on a buried insulator includes the steps of: forming one or more fins in a SOI layer of an SOI wafer, wherein the SOI wafer has a substrate separated from the SOI layer by the buried insulator; forming a SiGe layer on the fins; annealing the SiGe layer under conditions sufficient to drive-in Ge from the SiGe layer into the fins and form a SiGe shell completely surrounding each of the fins; and removing the fins selective to the SiGe shell, wherein the SiGe shell which remains forms the nanotubes on the buried insulator. A nanotube structure and method of forming a nanotube device are also provided.

20 Claims, 5 Drawing Sheets

(51) Int. Cl.
*G01N 33/00* (2006.01)
*B82Y 15/00* (2011.01)
*B82Y 40/00* (2011.01)

(56) References Cited

U.S. PATENT DOCUMENTS

| | | |
|---|---|---|
| 8,349,667 B2 | 1/2013 | Saracco et al. |
| 8,384,069 B2 | 2/2013 | Pernel et al. |
| 2007/0157873 A1 | 7/2007 | Hauptmann et al. |
| 2010/0164102 A1* | 7/2010 | Rachmady ............. B82Y 10/00 257/741 |
| 2011/0147697 A1* | 6/2011 | Shah ...................... B82Y 10/00 257/9 |
| 2011/0210309 A1* | 9/2011 | Ben-Ishai ............. B82Y 10/00 257/9 |
| 2012/0217468 A1 | 8/2012 | Tekleab et al. |
| 2014/0183452 A1* | 7/2014 | Hirai .................... H01L 29/778 257/24 |
| 2014/0231913 A1 | 8/2014 | Leobandung |
| 2014/0353577 A1 | 12/2014 | Agarwal et al. |
| 2015/0034834 A1 | 2/2015 | Afzali-Ardakani et al. |
| 2015/0115216 A1* | 4/2015 | Glass et al. ..... H01L 21/823431 257/9 |
| 2015/0214338 A1* | 7/2015 | Cheng ............... H01L 29/66795 257/194 |

OTHER PUBLICATIONS

S.Y. Jeong et al., "Synthesis of Silicon Nanotubes on Porous Alumina Using Molecular Beam Epitaxy," Advanced Materials, vol. 15, issue 14, pp. 1172-1176 (Jul. 2003).

J. Sha et al., "Silicon Nanotubes," Advanced Materials, vol. 14, issue 17, pp. 1219-1221 (Sep. 2002).

V.Y. Prinz et al., "Free-standing and overgrown InGaSa/GaAs nanotubes, nanohelices and their arrays," Physica E 6, pp. 828-831 (Feb. 2000).

Zang et al., "Mechanism for Nanotube Formation from Self-Bending Nanofilms Driven by Atomic-Scale Surface-Stress Imbalance," Physical Review Letters 98, 146102 (Apr. 2007).

Kong et al., "Nanotube Molecular Wires as Chemical Sensors," Science, vol. 287, pp. 622-625 (Jan. 2000).

* cited by examiner

FORMATION OF SIGE NANOTUBES

FIELD OF THE INVENTION

The present invention relates to techniques for forming nanostructured materials, and more particularly, to the formation of silicon germanium (SiGe) nanotubes.

BACKGROUND OF THE INVENTION

Unlike carbon nanotubes, nanostructures of germanium, a group IV semiconductor, have not been fully explored. Germanium and associated compounds at nanoscale are promising candidates for future nanoelectronics based technologies, e.g., nanotube metal oxide semiconductor field effect transistor (MOSFET) devices, which can extend the device scaling roadmap while maintaining good short channel effects and providing competitive drive current.

Techniques for forming nanotubes from a thin solid film of material have been proposed. See, for example, Schmidt et al., "Nanotechnology: Thin solid films roll up into nanotubes," Nature 410, 168 (March 2001) which describes a process by which films that are released from a substrate roll up into the shape of a nanotube. It is however difficult to achieve nanotubes with consistent dimensions using this type of process, and the process is not efficient enough for large-scale production.

Therefore, improved techniques for producing nanostructured materials would be desirable.

SUMMARY OF THE INVENTION

The present invention provides techniques for forming nanostructured materials such as silicon germanium (SiGe) nanotubes. In one aspect of the invention, a method for forming nanotubes on a buried insulator is provided. The method includes the steps of: forming one or more fins in a silicon-on-insulator (SOI) layer of an SOI wafer, wherein the SOI wafer has a substrate separated from the SOI layer by the buried insulator; forming a SiGe layer on the fins; annealing the SiGe layer under conditions sufficient to drive-in germanium (Ge) from the SiGe layer into the fins and form a SiGe shell completely surrounding each of the fins; and removing the fins selective to the SiGe shell, wherein the SiGe shell which remains forms the nanotubes on the buried insulator.

In another aspect of the invention, a nanotube device is provided. The nanotube device includes: one or more nanotubes on a buried insulator prepared by the above method.

In yet another aspect of the invention, a method of forming a nanotube device is provided. The method includes the steps of: forming one or more fins in a SOI layer of an SOI wafer, wherein the SOI wafer has a substrate separated from the SOI layer by a buried insulator; forming a SiGe layer on the fins; annealing the SiGe layer under conditions sufficient to drive-in Ge from the SiGe layer into the fins and form a SiGe shell completely surrounding each of the fins; removing the fins selective to the SiGe shell, wherein the SiGe shell which remains forms the nanotubes on the buried insulator; and forming contacts to opposite ends of at least one of the nanotubes.

A more complete understanding of the present invention, as well as further features and advantages of the present invention, will be obtained by reference to the following detailed description and drawings.

DETAILED DESCRIPTION OF PREFERRED EMBODIMENTS

Provided herein are techniques for forming silicon-germanium (SiGe) nanotubes using semiconductor lithography techniques. As will be described in detail below, the present techniques generally involve forming silicon (Si) fins covered with a conformal SiGe layer, and then using an anneal to drive in germanium (Ge) from the SiGe layer into the fins to form a continuous SiGe shell surrounding each of the fins. Selectively removing the Si from the fins results in a hollow SiGe shell which is a nanotube structure. The present SiGe nanotube structures can be used in a variety of different device configurations. For illustrative purposes only, an exemplary chemical sensor device employing the present SiGe nanotubes is presented and described below.

Advantageously, the present techniques are completely compatible with the current complementary metal oxide semiconductor (CMOS) processes. The present SiGe nanotube arrays can be patterned on a substrate using standard lithography and etching techniques. Further, there are no alignment issues as compared with carbon nanotube field effect transistors.

Figure 1:
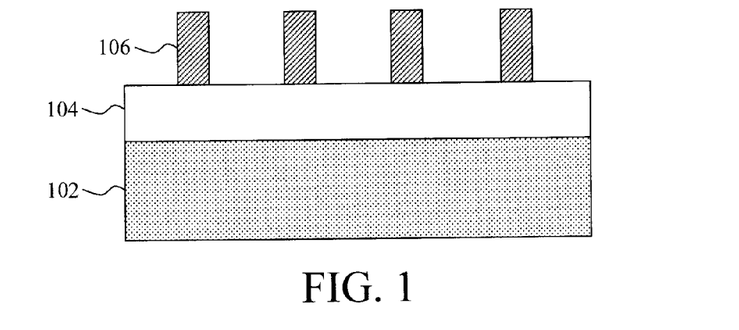
FIG. 1 is a cross-sectional diagram illustrating a starting platform for forming silicon germanium (SiGe) nanotubes including a silicon-on-insulator (SOI) wafer having a SOI layer separated from a substrate by a buried insulator, and a plurality of fins having been patterned into the SOI layer according to an embodiment of the present invention.

The present techniques are now described in detail by way of reference to FIGS. 1-9. As shown in FIG. 1, the starting platform for the present process is a silicon-on-insulator (SOI) wafer. As is known in the art, an SOI wafer includes a SOI layer separated from a substrate (e.g., substrate 102) by a buried insulator (e.g., buried insulator 104). See FIG. 1. Suitable substrate materials include, but are not limited to, silicon (Si), strained Si, silicon carbide (SiC), germanium (Ge), silicon germanium (SiGe), silicon-germanium-carbon (SiGeC), Si alloys, Ge alloys, gallium arsenide (GaAs), indium arsenide (InAs), indium phosphide (InP), or any combination thereof. Suitable dielectric materials for the buried insulator 104 include, but are not limited to, an oxide material such as silicon dioxide ($SiO_2$). When the buried insulator is an oxide, the buried insulator may also be referred to as a buried oxide or BOX.

As shown in FIG. 1, the SOI layer has been patterned into one or more fins 106. By way of example only, fins 106 may be patterned in the SOI layer directly using standard lithography and etching techniques. For instance, hardmask (not shown) may be formed on the SOI layer patterned with the footprint and location of the fins 106. An etching process, such as reactive ion etching (RIE) may then be used to pattern fins through the hardmask. Following the fin etch, any remaining hardmask is preferably removed. The buried insulator 104 can serve as an etch stop during the fin RIE.

Alternative processes for patterning the fins can include, for example, a sidewall image transfer process or SIT. SIT is useful for scaling purposes as it can be used to achieve sub-lithographic fin pitches. As is known in the art, SIT involves first patterning a mandrel (not shown) on the wafer, and then forming spacers (not shown) on opposite sides of the mandrel. The mandrel is removed selective to the spacers, and the spacers are used to pattern fins in the wafer. Thus, the pitch of the fins is doubled as compared to the pitch of the patterned mandrels. Suitable SIT techniques for fin patterning which may be used in accordance with the present techniques are described, for example, in U.S. Patent Application Publication Number 20140231913 by Effendi Leobandung, entitled "Trilayer SIT Process with Transfer Layer for FINFET Patterning," the contents of which are incorporated by reference as if fully set forth herein.

Figure 2:
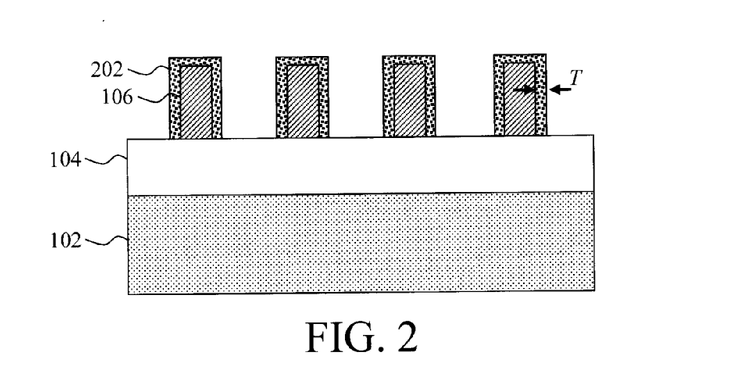
FIG. 2 is a cross-sectional diagram illustrating a layer of (e.g., epitaxial) SiGe having been formed covering (i.e., the tops and sidewalls of) the fins according to an embodiment of the present invention.

Next, as shown in FIG. 2, a layer of SiGe 202 is formed covering the fins 106. As shown in FIG. 2, the SiGe layer 202 may be formed as a conformal layer over the fins. However, that is merely an example, and it is not a requirement for SiGe layer 202 to conform to the shape of the fins. According to an exemplary embodiment, the SiGe layer 202 is epitaxially grown on the exposed surfaces of the fins 106. Epitaxial SiGe can be grown to a uniform thickness T on the exposed surfaces of the fins 106. It is notable that the thickness of the SiGe layer 202 will impact the thickness of the walls of the final SiGe nanotubes formed. Namely, as highlighted above, and as will be described in detail below, the SiGe shell surrounding the fins will serve as the walls of the resulting nanotubes. Thus, a greater amount of SiGe formed/grown at this stage will result in a thicker shell being formed surrounding each fin. According to an exemplary embodiment, T is from about 1 nanometers (nm) to about 100 nm, and ranges therebetween.

As shown in FIG. 2, since the base of the fins are attached to the buried insulator, the SiGe layer 202 is now only present on the tops and sidewalls of the fins. The goal is to be able to form a continuous SiGe shell completely surrounding each of the fins. To have complete access around a fin structure, e.g., to form a gate-all-around device, some conventional processes will suspend the structure by undercutting and/or removing material from beneath the structure. However, this can impact its mechanical stability, and higher aspect ratio structures will experience unacceptable levels of sagging as a result. Advantageously, the present process involves forming a SiGe shell via a drive in anneal all while the fins 106 remain tethered to the buried insulator 104. As a result, no loss of mechanical stability occurs during the process.

Figure 3:
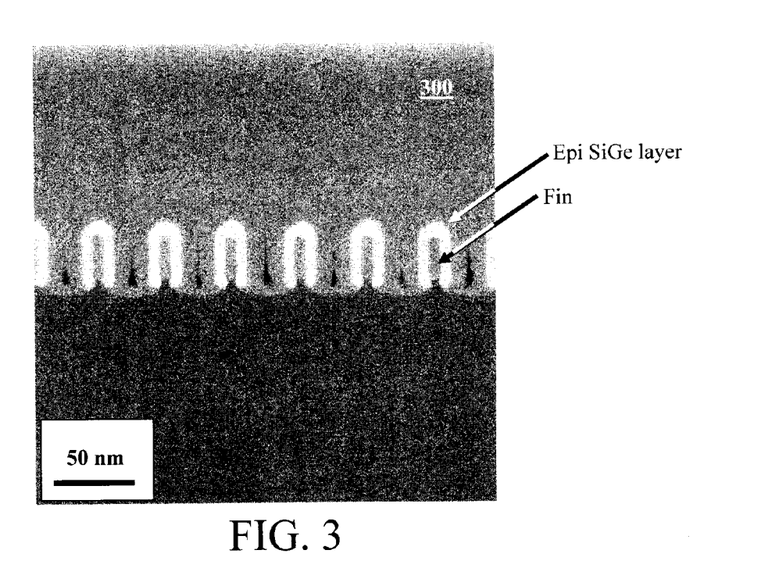
FIG. 3 is an image of a sample of the device structure following epitaxial growth of the SiGe layer on the tops and sidewalls of fins according to an embodiment of the present invention.

Referring briefly to FIG. 3, an image 300 is shown of a sample of the device structure following epitaxial growth of SiGe layer 202 on the tops and sidewalls of fins 106. The SiGe layer 202 appears as the white layer in the image covering each of the fins.

Figure 4:
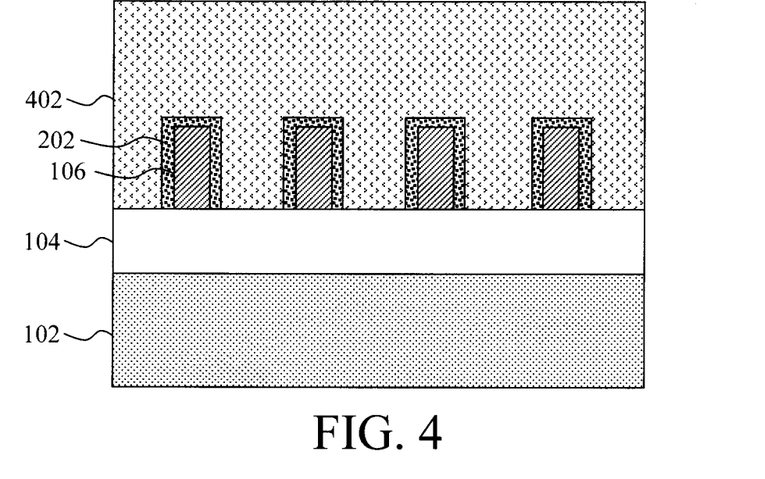
FIG. 4 is a cross-sectional diagram illustrating the fins having been buried in a dielectric material according to an embodiment of the present invention.

Returning to the process flow, as shown in FIG. 4 the fins 106 are buried in a dielectric material 402. According to an exemplary embodiment, the dielectric material 402 is an oxide, such as silicon dioxide ($SiO_2$). Dielectric material 402 may be deposited using a process such as chemical vapor deposition (CVD). For scaled fin pitches (e.g., below 50 nm), one might instead choose a process such as high density plasma (HDP) based on its better gap fill properties as compared to CVD.

As shown in FIG. 4, the dielectric material 402 completely buries the fins 106, i.e., the dielectric material 402 completely fills in the spaces between the fins 106, as well as a space above the tops of the fins 106. The dielectric material 402 deposited in this manner will serve to provide mechanical support for the fins 106 during the subsequent annealing process used to drive-in Ge from the SiGe layer 202 into the Si fins 106—see below.

Namely, the device structure is annealed in the presence of a gas selected from the group consisting of: hydrogen ($H_2$), oxygen ($O_2$), nitrogen ($N_2$), argon (Ar), helium (He), and combinations thereof, under conditions sufficient to drive in Ge from the SiGe layer 202 into the fins 106 and form a SiGe shell 502 completely surrounding each of the fins 106. See FIG. 5. According to an exemplary embodiment, the conditions for this drive in anneal include, but are not limited to, a temperature of from about 400° C. to about 1200° C., and ranges therebetween, for a duration of from about 1 millisecond to about 60 minutes, and ranges therebetween.

Namely, the Ge atoms driven in from SiGe layer 202 will react with the Si atoms in the fins 106 to form a layer of SiGe (i.e., the SiGe shell 502) at the surfaces of the fins 106. In addition to at the top and sidewalls of the fins, advantageously the SiGe shell will also form at the bottom of the fins. See FIG. 5. As a result, each of the fins 106 will be completely surrounded by the SiGe shell 502. The shell is formed along the bottom surface of the fins due to enhanced diffusion of Ge along the fin/buried insulator interface. In other words, Ge diffuses much faster along that interface than in the bulk fin. For example, the Ge diffusion rate can be at least 2 times the diffusion rate into bulk silicon (SOI in this case).

Following the drive-in anneal, the dielectric material 402 is removed from the fins 106. As provided above, the dielectric material 402 can be formed from an oxide material. Thus, in that case, the dielectric material 402 can be removed selective to the fins using an oxide-selective etching process, such as an oxide-selective RIE chemistry. Removal of the dielectric material 402 is necessary to enable further processing of the fins into the nanotubes (see below).

Figure 6:
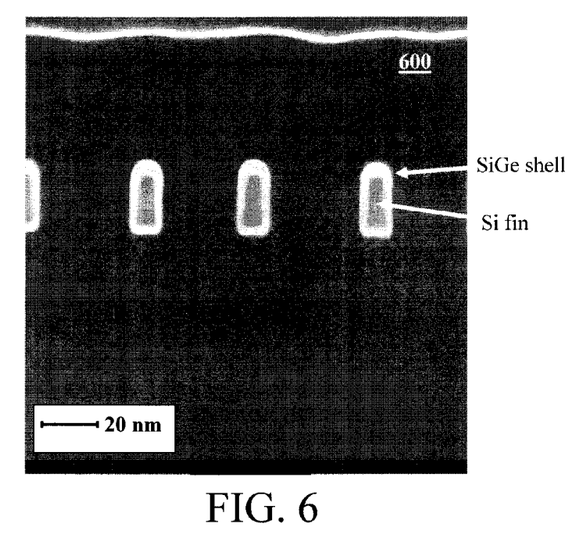
FIG. 6 is an image of a sample of the device structure following formation of the SiGe shell around each of the fins according to an embodiment of the present invention.

Referring briefly to FIG. 6, an image 600 is shown of a sample of the device structure following formation of the SiGe shell 502 around each of the fins 106. The SiGe shell 502 appears as the white layer in the image. As the image shows, the SiGe shell 502 completely surrounds each of the fins 106.

Figure 7:
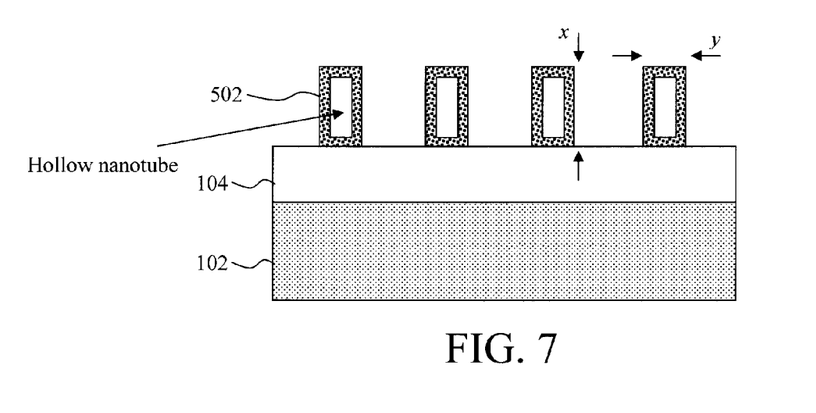
FIG. 7 is a cross-sectional diagram illustrating the remaining portions of the fins having been removed selective to the SiGe shell to form SiGe nanotubes according to an embodiment of the present invention.

Returning to the process flow, as shown in FIG. 7 in order to form the (SiGe) nanotubes, the remaining portions of the fins are removed selective to the SiGe shell 502. At this stage in the process, the fins are composed of Si (i.e., from the SOI layer) remaining after the drive-in anneal. By way of example only, the Si fin (core) may be removed selective to the SiGe shell 502 using a suitable wet selective etching process. For instance, a suitable wet etching method includes an aqueous solution containing ammonia. Access to the fin core can be achieved by performing a fin cut (e.g., a RIE etching process) to chop off the two ends of the core/shell structure to expose the Si core with the SiGe shell surrounding it.

The result of this selective fin etch is a plurality of hollow core SiGe nanotubes. See FIG. 7. As also shown in FIG. 7, due to the nature of the process the present nanotubes can have a unique shape based on the shape of the starting fin. For instance, in the example depicted in FIG. 7 (based on a starting fin shape that is a rectangle) each of the nanotubes when viewed in cross-section (i.e., what is shown in FIG. 7—through a plane perpendicular to the length of the nanotube) can have a rectangular shape with two sides having a length x and two sides having a lengthy. In one exemplary embodiment, x>y. In another exemplary embodiment, x=y and the nanotubes have a square cross-sectional shape (i.e., a square is a rectangle with sides of equal length). The ratio of x to y can be controlled based on the starting dimensions of the fins 106. Thus, advantageously, SiGe nanotubes can be formed on tall Si fins which have enhanced mobility performance and higher drive current per unit footprint area. The depiction of a rectangle (e.g., square) cross-sectional shape is merely one possible nanotube shape anticipated herein. Based on the shape of the starting fin, the present nanotubes can be produced having a variety of different shapes. By way of example only, in addition to a rectangular or square cross-sectional shape, the nanotubes might have a trapezoidal (i.e., a four sided shape with straight edges with a pair of parallel sides) cross-sectional shape.

Figure 5:
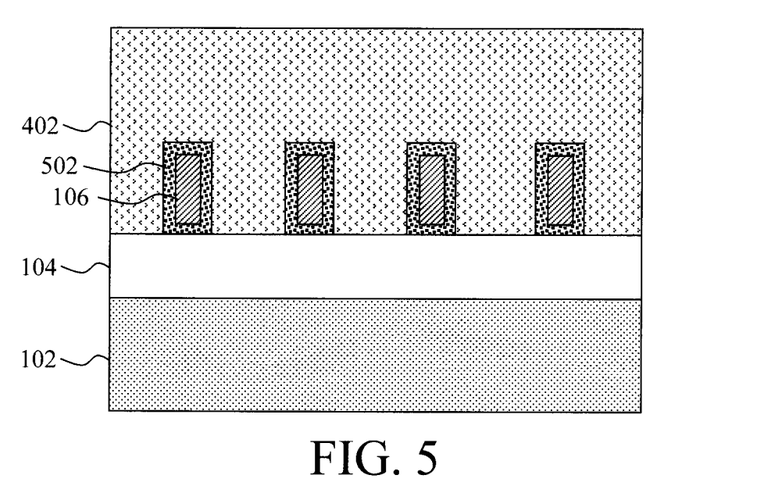
FIG. 5 is a cross-sectional diagram illustrating the device structure having been annealed under conditions sufficient to drive in germanium (Ge) from the SiGe layer into the fins, forming a SiGe shell completely surrounding each of the fins according to an embodiment of the present invention.
Figure 8:
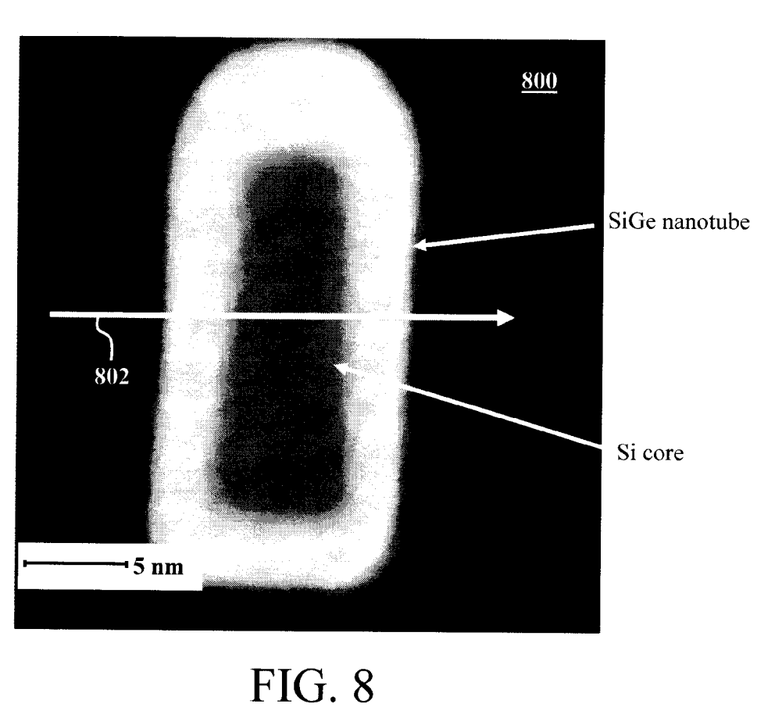
FIG. 8 is an enlarged image of a sample of the present SiGe shell and Si core device structure according to an embodiment of the present invention.

An enlarged image 800 of a SiGe shell and Si core structure (i.e., the intermediary product of the present techniques after the drive in anneal—see description of FIG. 5 above) is provided in FIG. 8. FIG. 8 is used to illustrate the effectiveness of the drive in anneal to form the SiGe shell completely surrounding the Si fin. Namely, in FIG. 8 the SiGe shell appears as the white layer in the image. The compositional profile of the core/shell structure is further demonstrated by way of reference to FIG. 9.

Figure 9:
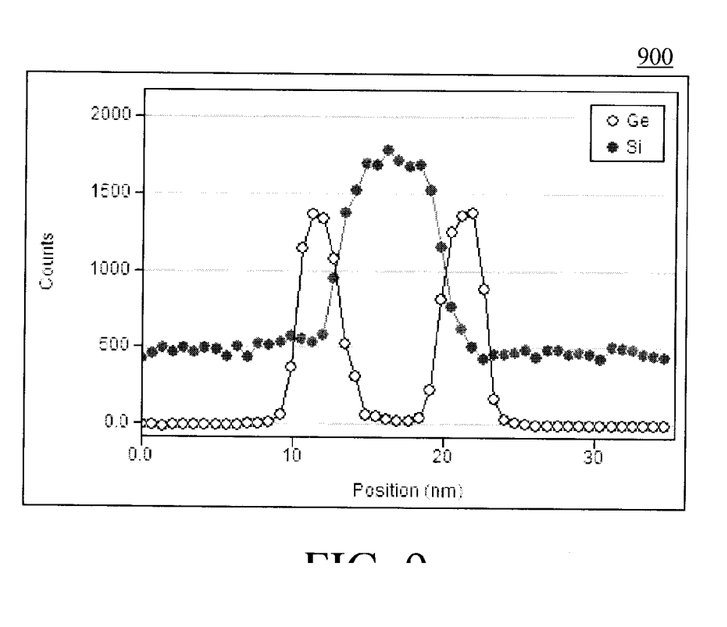
FIG. 9 is a plot illustrating the compositional profile of the SiGe shell and Si core structure of FIG. 8 according to an embodiment of the present invention.

Specifically, the compositional profile of the core/shell structure taken along the direction of arrow 802 (see FIG. 8) is represented by the plot 900 shown in FIG. 9. Specifically, in FIG. 9 the position (through the center of the core/shell structure—see arrow 802 in FIG. 8)—measured in nanometers (nm) is plotted on the x-axis and the Si and/or Ge counts are plotted on the y-axis. Arrow 802 in FIG. 8 indicates that the compositional profile is being taken as one moves from the shell to the core on one side of the structure, and then from the core back to the shell on the other side of the structure. Thus, as shown in FIG. 9 when passing through the shell (i.e., at from about 10 nm to about 15 nm along arrow 802) the structure contains both Si and Ge indicative of a SiGe containing shell. As one moves into the core (i.e., at from about 15 nm to about 20 nm along arrow 802) the Si content spikes and the Ge content drops nearly to 0 which is indicative of a Si core. Then as one passes from the core to the shell on the other side of the structure (i.e., at from about 20 nm to about 25 nm along arrow 802) the structure again contains both Si and Ge indicative of a SiGe containing shell. The Si content outside both sides of the shell is the result of the drive in anneal where Ge from the conformal SiGe layer is driven into the fin, leaving Si behind an Si-rich layer.

The present (SiGe) nanotubes can be used for a wide variety of different applications employing semiconductor nanostructured materials. By way of example only, one non-limiting exemplary implementation of the present techniques is in the fabrication of nanotube devices, such as SiGe nanotube-based sensors. See FIG. 10.

The use of nanostructured materials in sensor/detector devices has been demonstrated. See, for example, U.S. Patent Application Publication Number 2015/0034834 by Afzali-Ardakani et al., entitled "Radiation Detector Based on Charged Self-Assembled Monolayer on Nanowire Devices" (hereinafter "U.S. Patent Application Publication Number 2015/0034834"), the contents of which are incorporated by reference as if fully set forth herein. As described in U.S. Patent Application Publication Number 2015/0034834, the transconductance of the nanowire devices changes when a subject of detection (in this case radiation) is present. Advantageously, by being able to employ nanotube structures (rather than, e.g., nanowires) one can increase the sensitivity of the respective sensor/detector based on the increased surface area for detection along the outer surfaces of the nanotube as well as through the hollow core.

Figure 10:
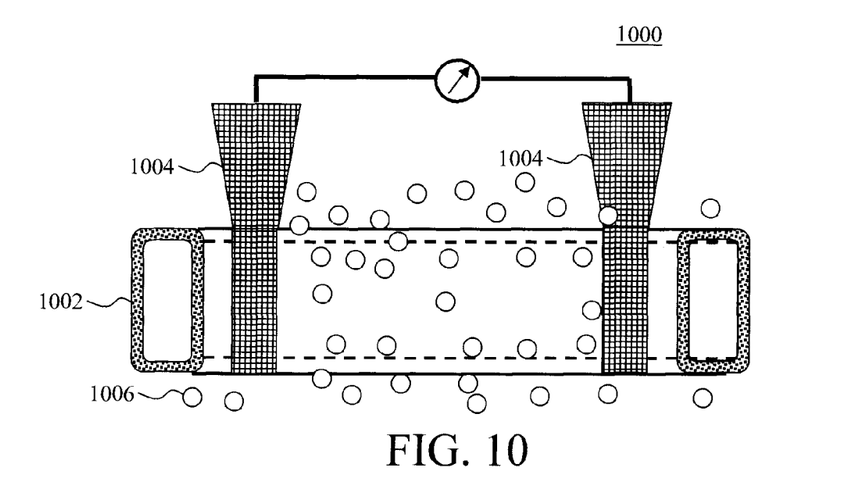
FIG. 10 is a diagram illustrating a (SiGe) nanotube-based sensor according to an embodiment of the present invention.

Referring now to FIG. 10, a (SiGe) nanotube-based sensor 1000 is shown. The sensor 1000 includes at least one SiGe nanotube 1002 and contacts 1004 formed to opposite ends of the SiGe nanotube 1002. The SiGe nanotube 1002 is formed by way of the present process which is described in detail above. It is notable that the perspective of the nanotube 1002 in FIG. 10 is along its length, whereas the figures described above depicting the fabrication process show cross-sections of the nanotube (i.e., cross-sections through a plane perpendicular to the length of the nanotubes). It is also notable that, while the example in FIG. 10 uses a single nanotube 1002 this is meant merely to illustrate the present techniques, and embodiments are anticipated herein where multiple nanotubes are employed in the device in the same manner as shown/described.

According to an exemplary embodiment, contacts 1004 are metal contacts. Suitable contact metals include, but are not limited to, copper (Cu), tungsten (W), tantalum (Ta), titanium (Ti), palladium (Pd), etc. Metal contacts can be formed to the nanotube(s) using conventional deposition techniques, such as evaporation, sputtering, electrochemical plating, etc.

As shown in FIG. 10, during operation the resistance of the nanotube 1002 is measured via contacts 1004. When present, target molecules 1006 adsorb onto the inner and the outer surfaces of the nanotube 1002, inducing carriers in the SiGe nanotubes and changing the conductivity of the nanotube 1002. By measuring the resistance change of the SiGe nanotube 1002 (via contacts 1004) and controlling the flow rate of the molecules 1006, one can sense the charges of the molecules. Further, as highlighted above, allowing molecules inside and outside of the nanotube 1002 enhances the sensitivity of the sensor. By way of example only, the present nanotube sensor can be used to measure gas molecules such as $NO_2$ and $NH_3$. See, for example, Kong et al., "Nanotube Molecular Wires as Chemical Sensors," Science, vol. 287, pgs. 622-625 (January 2000), the contents of which are incorporated by reference as if fully set forth herein.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method for forming nanotubes on a buried insulator, the method comprising the steps of:
    forming one or more fins in a silicon-on-insulator (SOI) layer of an SOI wafer, wherein the SOI wafer has a substrate separated from the SOI layer by the buried insulator;
    forming a silicon germanium (SiGe) layer on the fins;
    annealing the SiGe layer under conditions sufficient to drive-in germanium (Ge) from the SiGe layer into the fins and form a SiGe shell completely surrounding each of the fins; and
    removing the fins selective to the SiGe shell, wherein the SiGe shell which remains forms the nanotubes on the buried insulator.

2. The method of claim 1, wherein the SiGe layer comprises epitaxial SiGe, the method further comprising the step of:
    growing the SiGe layer on the fins.

3. The method of claim 1, wherein the conformal SiGe layer has a thickness T of from about 1 nanometers (nm) to about 100 nm, and ranges therebetween.

4. The method of claim 1, wherein the conditions comprise a temperature of from about 400° C. to about 1200° C., and ranges therebetween.

5. The method of claim 1, wherein the conditions comprise a duration of from about 1 millisecond to about 60 minutes, and ranges therebetween.

6. The method of claim 1, wherein the annealing is performed in the presence of a gas selected from the group consisting of: oxygen ($O_2$), hydrogen ($H_2$), nitrogen ($N_2$), argon (Ar), helium (He), and combinations thereof.

7. The method of claim 1, further comprising the step of:
    burying the fins in a dielectric material before the annealing.

8. The method of claim 7, wherein the dielectric material comprises an oxide material.

9. The method of claim 7, further comprising the step of:
    removing the dielectric material before removing the remaining portions of the fins selective to the SiGe shell.

10. The method of claim 1, wherein the remaining portions of the fins are removed selective to the SiGe shell using a silicon-selective wet etch with an aqueous solution containing ammonia.

11. A device comprising one or more nanotubes on a buried insulator prepared by the method of claim 1.

12. The nanotube device of claim 11, wherein each of the nanotubes comprises two sides having a length x and two sides having a length y, wherein x=y.

13. The nanotube device of claim 11, wherein each of the nanotubes comprises two sides having a length x and two sides having a length y, wherein x>y.

14. The nanotube device of claim 11, wherein the nanotube device comprises a sensor, the nanotube device further comprising:
    contacts to opposite ends of at least one of the nanotubes.

15. A method of forming a nanotube device, the method comprising the steps of:
    forming one or more fins in a SOI layer of an SOI wafer, wherein the SOI wafer has a substrate separated from the SOI layer by a buried insulator;
    forming a SiGe layer on the fins;
    annealing the SiGe layer under conditions sufficient to drive-in Ge from the SiGe layer into the fins and form a SiGe shell completely surrounding each of the fins;
    removing the fins selective to the SiGe shell, wherein the SiGe shell which remains forms the nanotubes on the buried insulator; and
    forming contacts to opposite ends of at least one of the nanotubes.

16. The method of claim 15, wherein the conditions comprise a temperature of from about 400° C. to about 1200° C., and ranges therebetween.

17. The method of claim 15, wherein the conditions comprise a duration of from about 1 millisecond to about 60 minutes, and ranges therebetween.

18. The method of claim 15, wherein the annealing is performed in the presence of a gas selected from the group consisting of: $O_2$, $H_2$, $N_2$, Ar, He, and combinations thereof.

19. The method of claim 15, further comprising the steps of:
    burying the fins in a dielectric material before the annealing; and
    removing the dielectric material before removing the remaining portions of the fins selective to the SiGe shell.

20. A nanotube device prepared by the method of claim 15.

* * * * *